United States Patent [19]

Rambert et al.

[11] 4,001,897

[45] Jan. 11, 1977

[54] PROSTHESIS FOR A JOINT

[76] Inventors: Andre Rambert, Residence Florentine Avenue Lacassagne, Lyon 3eme, Rhone, France; Gilles Bousquet, 19 Avenue Berranger, Ecully, Rhone, France

[22] Filed: Jan. 27, 1976

[21] Appl. No.: 652,810

[30] Foreign Application Priority Data

Jan. 31, 1975  France .............................. 75.03645

[52] U.S. Cl. .............................. 3/1.913; 128/92 C; 128/92 CA
[51] Int. Cl.² .......................................... A61F 1/24
[58] Field of Search ............................ 3/1.9–1.913, 3/1; 128/92 C, 92 CA

[56] References Cited

UNITED STATES PATENTS 3,813,699   6/1974   Giliberty .............................. 3/1.912
3,894,297   7/1975   Mittelmeier et al. ............... 3/1.912

*Primary Examiner*—Ronald L. Frinks
*Attorney, Agent, or Firm*—Browdy and Neimark

[57] ABSTRACT

A partial prosthesis for a joint designed to replace the head of a femur. A spherical head integral with a pin, which is designed to engage the femur, when in its utilization position engages a spherical cap which is to be accommodated and supported in the acetabulum of a hip. The cap has an inside spherical bearing surface of given diameter to assure that the spherical head has great freedom of movement therein and, at its base, an internal cylindrical shoulder small in width and of a diameter slightly smaller than the spherical bearing surface.

5 Claims, 2 Drawing Figures

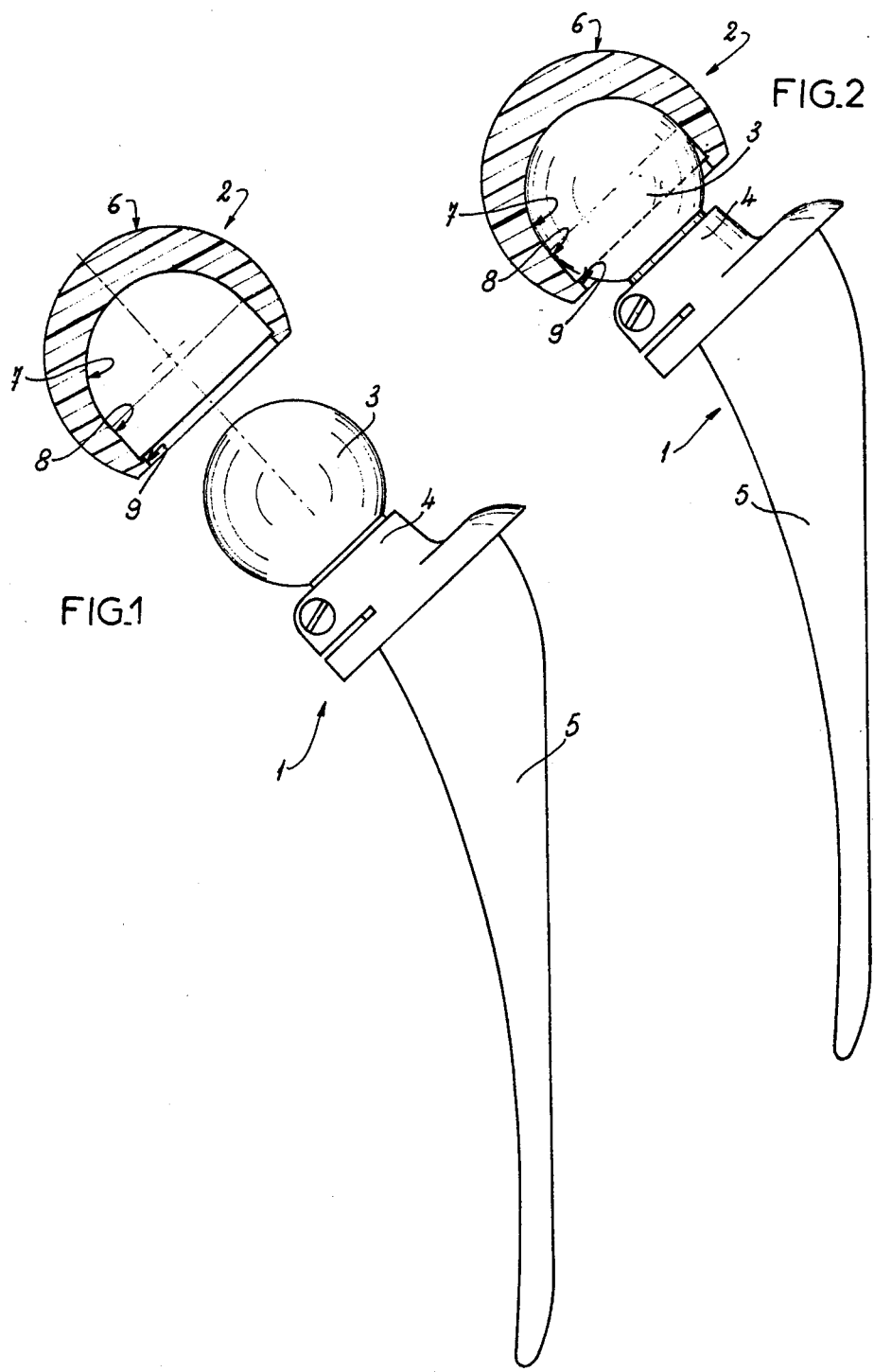

PROSTHESIS FOR A JOINT

BACKGROUND OF THE INVENTION

This invention relates to a prosthesis for a joint and, more particularly but not exclusively to a partial hip prosthesis.

It is known that partial hip prostheses in general have a femoral part which includes a femoral head connected to a rod or a pin able to be engaged into the femur, the femoral head being designed to engage and pivot in the acetabulum in the manner of a ball-and-socket joint.

Such known prostheses are made either entirely of metal or of metal and plastic. In the latter case a spherical plastic cap is applied to the head of a metal femoral part.

It has become known that friction of a metal or plastic foreign body, such as results from use of these known prostheses, entails a number of disadvantages such as pain, wear of the cartilage, or even penetration by the inert material into the cartilage and into the subchondral bone.

Among known partial prostheses, there are some which have a cap not sealed into the pelvis and which is held on the spherical head of the prosthesis by a joint which renders the cap immobile. On the other hand, this cap is mounted fairly firmly on the spherical bearing surface of the femoral part of the prosthesis and most of the movement will occur, not between the inert parts of the prosthesis, but between the spherical cap and the cartilage.

SUMMARY OF THE INVENTION

It is an object of the present invention to avoid the aforementioned disadvantages by providing a partial prosthesis in which most of the movement is to be affected between inert parts of the prosthesis.

It is another object of the present invention to provide a partial prosthesis in which most of the movement is effected between its spherical cap and its femoral head.

It is a further object of the present invention to provide a partial prosthesis which, when in place, need tolerate only small movements between its inert material and the cartilage of the organism, most of the movement occurring between the inert parts of the prosthesis.

It is an additional object of the present invention to provide a partial prosthesis which is easily stored.

The foregoing objects, as well as others which are to become clear from the text below, are achieved according to the present invention, by providing a partial prosthesis which is characterized by an element equivalent to the head of the femur. The partial prosthesis includes in combination, on the one hand, a spherical head integral with a pin designed to engage in a femur and, on the other hand, a spherical cap designed to be accommodated and bear on the acetabulum of a hip. Prior to use, the cap may be stored apart from its spherical head.

The removable nature of the cap with respect to the head considerably improves the storage conditions of the prosthesis of the present invention since, at the time of the surgical operation, one and the same head can receive the particular cap whose outer diameter matches the acetabulum of the patient. Before the operation, it will thus be sufficient to have available a metal part, constituting the head and the pin, and a complete set of caps instead of a complete set of heads, pins and caps.

In addition, the cap is very easily mounted on the spherical head, because this is done merely by applying pressure.

Another advantage of the present invention is to permit the cap to be replaced if it wears out without operating on the femur.

Finally, the metal part, the spherical head and pin, can be used as the femoral element of a full prosthesis whose cupula, intended to be sealed into the patient's acetabulum, would have a spherical bearing surface adapted to the spherical head of the metal part.

As a result, if the condition of the patient's acetabulum has advanced to the point where the partial prosthesis needs to be replaced by a full prosthesis, it would be sufficient to remove the cap and seal a cupula of a classic type into the patient's acetabulum, without operating on the femur.

According to one important feature of the invention, the spherical cap has, on the one hand, an interior spherical bearing surface of a diameter such as to provide the spherical head integral with the pin with great freedom of movement inside the spherical cap and, on the other hand, at its base a cylindrical inside shoulder of small width and of a diameter slightly less than the diameter of the spherical bearing surface. This great freedom of movement of the spherical head in its associated cap diminishes movements between the cap and the bottom of the acetabulum, the principal movement occuring between the spherical head and its associated cap.

According to another preferred feature of the invention, to enhance still further the degree of freedom of movement between the spherical head and the cap, a cylindrical portion of the cap coaxial with the spherical bearing surface and the shoulder, and of the same diameter as the spherical bearing surface, is arranged between the spherical head and the inside shoulder. This characteristic has the advantage of reducing risks of dislocation, due to the escape phenomenon of the spherical head on ths cylindrical portion of the cap.

BRIEF DESCRIPTION OF THE DRAWING

FIG. 1 is an exploded elevational view, partly in cross section, of a partial prosthesis according to a nonlimitative embodiment of the present invention.

FIG. 2 is a view similar to that of FIG. 1, showing the partial prosthesis of FIG. 1 in its utilization position.

DETAILED DESCRIPTION OF THE PREFERRED EMBODIMENT

As illustrated in FIGS. 1 and 2, an exemplary embodiment of a partial prosthesis according to the present invention is composed of two elements, namely a metal element 1 and a plastic head 2. The element 1, which is designed to be attached to the upper amputated end of the patient's femur, is composed, in a known manner, of a spherical head 3 integral with a rod or pin 5 designed to be anchored in the epiphysodiaphyseal cavity of the patient's femur. This spherical head 3 is preferably attached removably to the pin 5 by any appropriate means and, in particular, by engagement of a radial cylindrical projection integral with the head 3 in a collar 4 with which the upper end of pin 5 is provided. A bolt may be used to fix the collar 4 to the projection. Details of an attaching arrangement which may be used are described in French Patent No. 72/46,268 of Dec. 20, 1972.

The cap 2 is spherical in shape, having an outside spherical bearing surface 6 designed to be accommodated and supported in the acetabulum of a patient's hip and an inside spherical bearing surface 7 designed to receive the spherical head 3 of the element 1. The two bearing surfaces 6 and 7 are practically concentric.

The inside spherical bearing surface 7 is joined by a cylindrical portion 8 to a ledge or shoulder 9 small in width and slightly smaller in diameter than the spherical head 3. FIG. 2 illustrates that the shoulder 9 ensures that the spherical head 3 is held in place when the latter is engaged inside the spherical cap 2. However, the difference in diameter between the shoulder 9 and the spherical head 3 must be sufficient to permit placement and engagement of the head 3 in the cap 2 and disengagement thereof, as these operations must be executable merely by pressure. The material of which cap 2 is composed can be any material giving every satisfaction from the standpoints of function and tolerance by the organism which is to use the partial prothesis.

The diameter of spherical bearing surface 7 of the cap 2 is determined with respect to that of the spherical head 3 such that the latter has great freedom of movement after it has been mounted in the cap 2. The presence of the cylindrical portion part 8 of the cap 2 has the effect of increasing this great freedom of movement still further. As a result, most of the movement of the joint occurs between the spherical head 3 and the cap 2 and not between the outside, spherical bearing surface 6 of the cap 2 and the bottom of the acetabulum of the patient's hip. This has the effect of diminishing friction between the partial prosthesis of the present invention and the cartilage with which the bottom of this acetabulum is covered.

One of the essential advantages of the partial prosthesis of the present invention, in addition to its functional advantages, is that of considerably facilitating storage as a function of patient needs. In fact, one and the same metal element 1 can be used with any one of a complete set of spherical caps 2. Thus, instead of storing seven complete partial prostheses, it is sufficient to store one metal element 1 and several, for example seven, of the spherical caps 2; the surgeon is able to choose during the operation that particular spherical cap 2 having a spherical bearing surface 6 best fitted to the patient's acetabulum.

It is to be understood that after wear it is easy to replace the cap 2 with a new cap, a change which can obviously be effected without operating on the femur.

It must also be noted that the element 1 can constitute the femoral element of a total prosthesis whose spherical head 3 can be changed as needed. As a result, if the condition of the patient's acetabulum equipped with a partial prosthesis advances to the point where the partial prosthesis must be replaced by a full prosthesis, it is sufficient to remove the cap 2 and seal a cupula of conventional type, in particular of the type described in the above-mentioned French Patent No. 72/46,268 into the acetabulum of this patient. This replacement of a partial prosthesis by a full prosthesis can thus be accomplished without operating on the femur.

It is obvious that the invention is not confined to the single embodiment described hereinabove as a non-limiting example. On the contrary, the invention embraces numerous varients and embodiments, including those using equivalent features, its scope being defined in the appended claims.

What is claimed is:

1. A prosthesis for a joint comprising, in combination:
    a spherical head integral with a part which is to substitute for at least a portion of a bone, and
    a spherical cap which is to be accommodated and supported in a patient, said spherical cap having (1) an inside spherical bearing surface with a given diameter so as to ensure that said spherical head may be accommodated and have freedom of movement therein, (2) an internal cylindrical shoulder at its base, said shoulder being narrow in width and having a diameter slightly smaller than said given diameter, and (3) a portion defining an inner cylindrical surface co-axial with said bearing surface and adjacent said shoulder, said cylindrical surface being disposed between said shoulder and said spherical surface when in its utilization position.

2. A prosthesis for a joint according to claim 1, wherein said part which is to be substituted for at least a portion of a bone comprises a pin for engaging into a femur of a patient to provide a partial prosthesis.

3. A prosthesis for a joint according to claim 2, wherein its spherical cap comprises a spherical cap which can be accommodated and supported in the acetabulum of a hip of a patient.

4. A prosthesis for a joint according to claim 1, wherein its spherical cap comprises a spherical cap which can be accommodated and supported in the acetabulum of a hip of a patient.

5. A prosthesis for a joint according to claim 1, wherein said cylindrical surface co-axial with said bearing surface defines a cylinder having a diameter equal to said given diameter.

* * * * *